(12) United States Patent
Rich et al.

(10) Patent No.: US 7,328,722 B2
(45) Date of Patent: Feb. 12, 2008

(54) PULSATION ATTENUATOR FOR A FLUIDIC SYSTEM

(75) Inventors: Collin A. Rich, Ypsilanti, MI (US); Steven M. Martin, Ann Arbor, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 113 days.

(21) Appl. No.: 11/297,667

(22) Filed: Dec. 7, 2005

(65) Prior Publication Data
US 2007/0125436 A1   Jun. 7, 2007

(51) Int. Cl.
*F16L 55/04* (2006.01)
(52) U.S. Cl. .............................. 138/30; 138/31; 138/26
(58) Field of Classification Search .................. 138/26, 138/30, 31, 40, 41, 42
See application file for complete search history.

(56) References Cited

U.S. PATENT DOCUMENTS 3,672,402 A * 6/1972 Bloemer ..................... 138/31
6,039,078 A * 3/2000 Tamari ......................... 138/30
2002/0059959 A1 * 5/2002 Qatu et al. .................... 138/30

* cited by examiner

*Primary Examiner*—Patrick F. Brinson
(74) *Attorney, Agent, or Firm*—Jeffrey Schox

(57) ABSTRACT

A pulsation attenuator for a fluidic system with a fluidic pump. The pulsation attenuator includes a fluidic channel, a first fluidic device adapted to attenuate pulsations with a shallow rolloff slope, and a second fluidic device adapted to attenuate pulsations with a shallow rolloff slope. The first fluidic device and the second fluidic device are connected to the fluidic channel such that they cooperatively attenuate pulsations with a steep rolloff slope. Preferably, the first fluidic device includes a first fluidic resistor and a first fluidic capacitor, and the second fluidic device includes a second fluidic resistor and a second fluidic capacitor. Preferably, the pulsation attenuator is arranged, similar a second-order low-pass filter, in the following order: (1) first fluidic resistor, (2) first fluidic capacitor, (3) second fluidic resistor, and (4) second fluidic capacitor.

26 Claims, 2 Drawing Sheets

PULSATION ATTENUATOR FOR A FLUIDIC SYSTEM

DESCRIPTION OF THE PREFERRED EMBODIMENTS

The following description of the preferred embodiment of the invention is not intended to limit the invention to this preferred embodiment, but rather to enable any person skilled in the art of fluidic systems for flow cytometers to make and use this invention.

Figure 1:
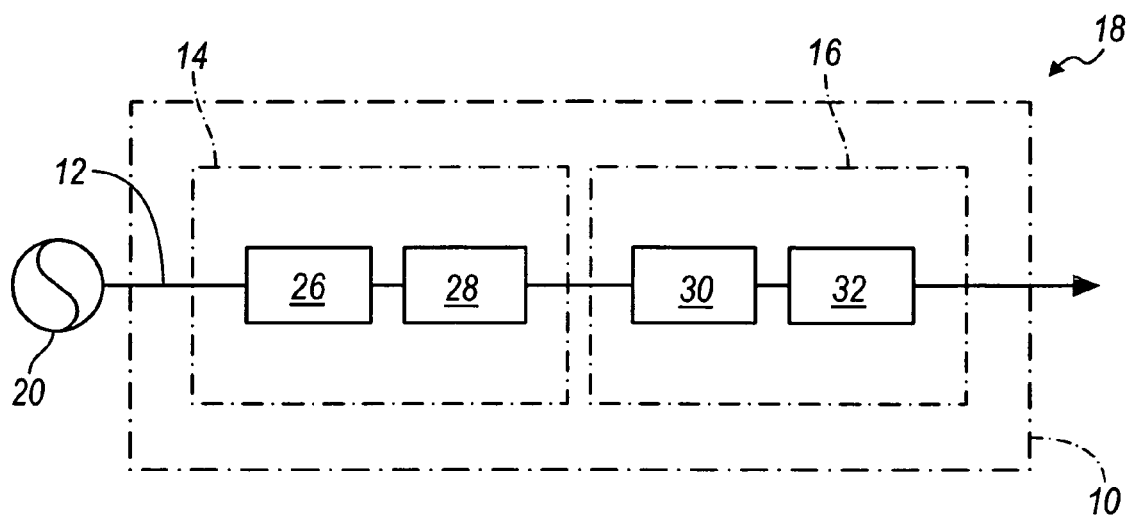
FIG. 1 is schematic representation of the pulsation attenuator of the preferred embodiment in a fluidic system with a fluidic pump.

As shown in FIG. 1, the pulsation attenuator 10 of the preferred embodiment includes a fluidic channel 12, a first fluidic device 14 adapted to attenuate pulsations, and a second fluidic device 16 adapted to attenuate pulsations. The pulsation attenuator 10 has been specifically designed for a fluidic system 18 of a flow cytometer with a fluidic pump 20, such as a peristaltic pump, but may be alternatively used in any suitable fluidic system.

Figure 2:
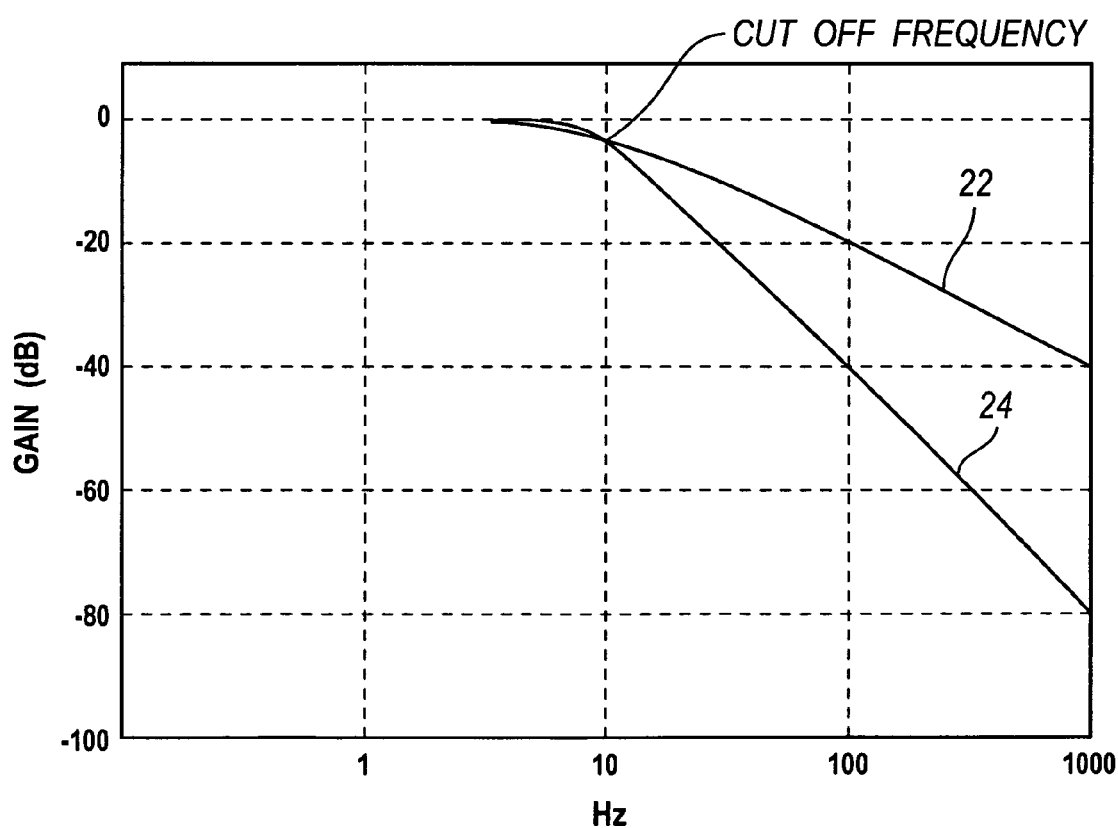
FIG. 2 is a Bode magnitude plot of the first and second fluidic devices and the combination of the first and second fluidic devices.

As shown in FIG. 2, the first fluidic device 14 and second fluidic device 16 of the preferred embodiment attenuate pulsations with a relatively shallow rolloff slope 22. For the purposes of this document, a shallow rolloff slope is defined as less than or equal to 20 dB/decade (as conventionally understood in a Bode magnitude plot of log magnitude against log frequency, and as displayed as the absolute value of the slope). The first fluidic device 14 and the second fluidic device 16 are connected to the fluidic channel 12, however, such that they preferably cooperatively attenuate pulsations with a relatively steep rolloff slope 24. For the purposes of this document, a steep rolloff slope 24 is defined as greater than 20 dB/decade (as conventionally understood in a Bode magnitude plot of log magnitude against log frequency, and as displayed as the absolute value of the slope). With a steep rolloff slope 24, such as greater than 20 dB/decade (or, more preferably, greater than or equal to 40 dB/decade), the pulsation attenuator 10 may be able to pass low-frequency fluctuations of the flow rate and filter high-frequency pulsations of the fluid within the fluidic channel 12. More significantly, the fluidic system may be able to rapidly adjust and stabilize the flow rate, while maintaining smooth flow. The rapid adjustment of the flow rate, which may have previously took several minutes in conventional fluidic systems and now could potentially take seconds, preferably minimizes the waste of the fluid within the fluidic system. The cutoff frequency is preferably less than or equal to 10 Hz and more preferably equal to 2 Hz, but may be any suitable cutoff frequency based on the needs of the fluidic system 18.

As shown in FIG. 1, the fluidic channel 12 of the preferred embodiment functions to carry fluid, such as a sample fluid, in the fluidic system 18. The fluid channel is preferably a rigid or flexible pipe, but may be any suitable fluidic device that carries fluid.

The first fluidic device 14 and the second fluidic device 16 of the preferred embodiment function to attenuate pulsations. For the purposes of this document, the term "pulsations" is defined as the periodic phenomenon that alternately increases and decreases either the pressure or flow rate of the fluid within the fluidic system. The first fluidic device 14 preferably includes a first fluidic resistor 26 and a first fluidic capacitor 28, and the second fluidic device 16 preferably includes a second fluidic resistor 30 and a second fluidic capacitor 32. In the preferred embodiment, for economic reasons, the first fluidic device 14 and the second fluidic device 16 are preferably substantially similar. In alternative embodiments, the first fluidic device 14 and the second fluidic device 16 may be different fluidic devices and/or may have different fluidic values.

Figure 3:
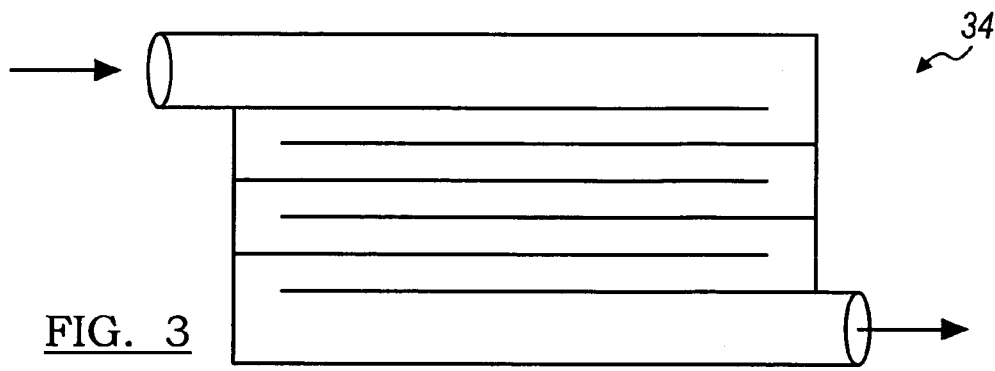
FIGS. 3 and 4 are variations of the fluidic resistors.
Figure 4:
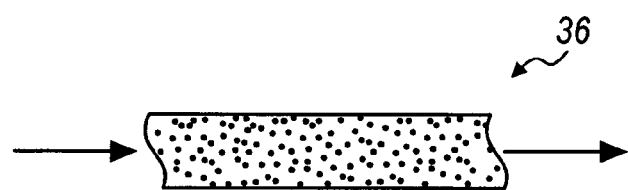

The first fluidic resistor 26 and the second fluidic resistor 30 function to resist the flow of the fluid within the fluidic channel 12. The first fluidic resistor 26 and the second fluidic resistor 30 are preferably a narrow-channel-type or a long-channel-type fluidic resistor 34 (which is shown in a space-saving serpentine-type arrangement in FIG. 3) or a ball-type fluidic resistor 36 (as shown in FIG. 4), but may be any suitable fluidic device to resist the flow of the fluid within the fluidic channel 12.

Figure 5:
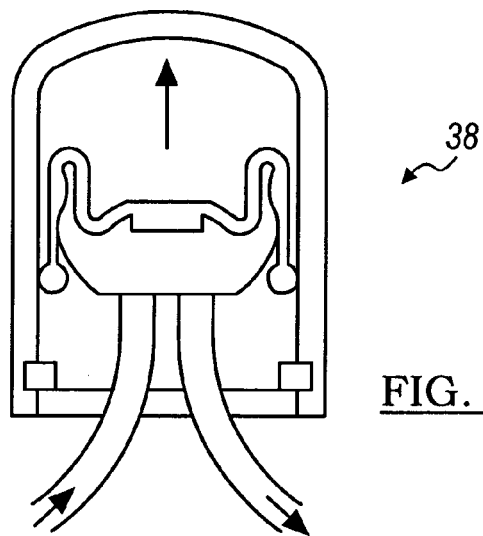
FIGS. 5 and 6 are variations of the fluidic capacitors.
Figure 6:
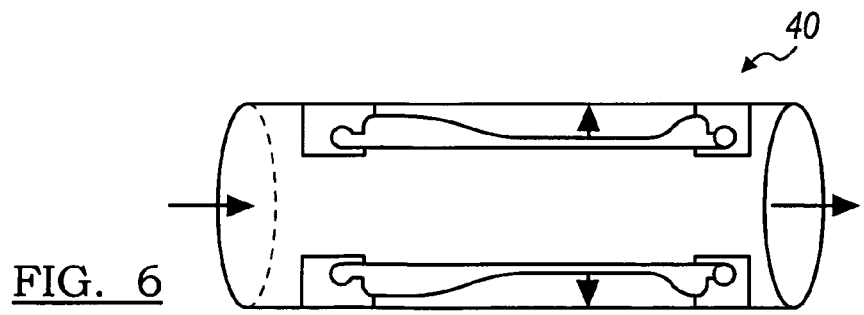

The first fluidic capacitor 28 and the second fluidic capacitor 32 function to temporarily expand and accumulate fluid (and, hence, pressure) within the fluidic channel 12 and to later contract and reintroduce the accumulated fluid (and, hence, pressure) to the fluidic channel 12. The first fluidic capacitor 28 and the second fluidic capacitor 32 are preferably a bellows-type fluidic capacitor 38 (as shown in FIG. 5) or a flexible tube-type fluidic capacitor 40 (as shown in FIG. 6), but may be any suitable fluidic device to temporarily expand and later contract. The bellows-type fluidic capacitor 38, for example, may be made without an actual diaphragm between the fluid of the fluidic channel and the compressible fluid (such as air) of the bellows-type fluidic capacitor 38. Instead of a diaphragm, the bellows-type fluidic capacitor 38 could rely on gravity or any other suitable method or device to keep the two fluids separate.

As shown in FIG. 1, the first fluidic device 14 and the second fluidic device 16 are preferably configured and arranged to attenuate pulsations above a cutoff frequency (similar to an electronic low-pass filter). More specifically, the first fluidic device 14 includes the first fluidic resistor 26 followed by the first fluidic capacitor 28, and the second fluidic device 16 includes the second fluidic resistor 30 followed by the second fluidic capacitor 32. Thus, the fluid flowing through the pulsation attenuator 10 encounters the following elements in this order: (1) the first fluidic resistor 26, (2) the first fluidic capacitor 28, (3) the second fluidic resistor 30, and (4) the second fluidic capacitor 32. In this arrangement, the pulsation attenuator 10 is similar to a second-order electronic low-pass filter with a rolloff slope of −40 dB/decade.

The pulsation attenuator 10 may, alternatively, include more than two fluidic devices. In a pulsation attenuator 10 that includes five fluidic devices, for example, the fluid encounters the following elements in this order: (1) the first fluidic resistor 26, (2) the first fluidic capacitor 28, (3) the second fluidic resistor 30, (4) the second fluidic capacitor 32, (5) a third fluidic resistor, (6) a third fluidic capacitor, (7) a fourth fluidic resistor, (8) a fourth fluidic capacitor, (9) a fifth fluidic resistor, and (10) a fifth fluidic capacitor. In this arrangement, the pulsation attenuator 10 is similar to a fifth-order electronic low-pass filter with a rolloff of −100 dB/decade.

The first fluidic device 14 and the second fluidic device 16 may be alternatively configured and arranged to attenuate pulsations below a cutoff frequency (similar to an electronic high-pass filter). Further, the pulsation attenuator 10 of alternative embodiments may be arranged in any suitable order and may have any suitable number of fluidic devices, fluidic resistors, and fluidic capacitors, including a combination of a "low-pass" pulsation attenuator and a "high-pass" pulsation attenuator that would either attenuate pulsations within two frequencies (similar to an electronic band-stop filter) or outside of two frequencies (similar to an electronic band-pass filter).

As a person skilled in the art of fluidic systems for flow cytometers will recognize from the previous detailed description and from the figures and claims, modifications and changes can be made to the preferred embodiment of the invention without departing from the scope of this invention defined in the following claims.

We claim:

1. A pulsation attenuator for a fluidic system with a fluidic pump, comprising:
   a fluidic channel;
   a first fluidic device adapted to attenuate pulsations with a shallow rolloff slope; and
   a second fluidic device adapted to attenuate pulsations with a shallow rolloff slope;
   wherein the first fluidic device and the second fluidic device are connected to the fluidic channel such that they cooperatively attenuate pulsations with a steep rolloff slope.

2. A pulsation attenuator for a fluidic system with a fluidic pump, comprising:
   a fluidic channel;
   a first fluidic device connected to the fluidic channel and adapted to attenuate pulsations; and
   a second fluidic device connected to the fluidic channel and adapted to attenuate pulsations;
   wherein the first fluidic device and the second fluidic device are adapted to attenuate pulsations above a cutoff frequency.

3. The pulsation attenuator of claim 2, wherein the cutoff frequency is less than or equal to 10 Hz.

4. A pulsation attenuator for a fluidic system with a fluidic pump, comprising:
   a fluidic channel;
   a first fluidic device connected to the fluidic channel and adapted to attenuate pulsations; and
   a second fluidic device connected to the fluidic channel and adapted to attenuate pulsations;
   wherein the first fluidic device includes a first fluidic resistor and a first fluidic capacitor, and wherein the second fluidic device includes a second fluidic resistor and a second fluidic capacitor.

5. The pulsation attenuator of claim 4, wherein the first fluidic resistor and the second fluidic resistor include a serpentine-type fluidic resistor.

6. The pulsation attenuator of claim 4, wherein the first fluidic resistor and the second fluidic resistor include a ball-type fluidic resistor.

7. The pulsation attenuator of claim 4, wherein the first fluidic capacitor and the second fluidic capacitor include an accumulator-type fluidic capacitor.

8. The pulsation attenuator of claim 4, wherein the first fluidic capacitor and the second fluidic capacitor include a flexible tube-type fluidic capacitor.

9. The pulsation attenuator of claim 4, wherein the pulsation attenuator is arranged in the following order: (1) first fluidic resistor, (2) first fluidic capacitor, (3) second fluidic resistor, and (4) second fluidic capacitor.

10. A pulsation attenuator for a fluidic system with a fluidic pump, comprising:
    a fluidic channel;
    a first fluidic device adapted to attenuate pulsations with a shallow rolloff slope; and
    a second fluidic device adapted to attenuate pulsations with a shallow rolloff slope;
    wherein the first fluidic device and the second fluidic device are connected to the fluidic channel such that they cooperatively attenuate pulsations with a steep rolloff slope;
    wherein the first fluidic device is adapted to attenuate pulsations with a rolloff slope of less than or equal to 20 dB/decade, and the second fluidic device is adapted to attenuate pulsations with a rolloff slope of less than or equal to 20 dB/decade.

11. The pulsation attenuator of claim 10, wherein the first fluidic device and the second fluidic device are connected to the fluidic channel such that they cooperatively attenuate pulsations with a rolloff slope greater than 20 dB/decade.

12. The pulsation attenuator of claim 11, wherein the first fluidic device and the second fluidic device are connected to the fluidic channel such that they cooperatively attenuate pulsations with a rolloff slope greater than or equal to 40 dB/decade.

13. A fluidic system for a flow cytometer comprising: a fluidic pump and the pulsation attenuator of claim 1.

14. The fluidic system of claim 13 wherein the pump is a peristaltic pump.

15. A fluidic system for allow cytometer comprising:
    a fluidic pump;
    a fluidic channel;
    a first fluidic device adapted to attenuate pulsations with a shallow rolloff slope; and
    a second fluidic device adapted to attenuate pulsations with a shallow rolloff slope;
    wherein the first fluidic device and the second fluidic device are connected to the fluidic channel such that they cooperatively attenuate pulsations with a steep rolloff slope;
    wherein the first fluidic device and the second fluidic device are adapted to attenuate pulsations above a cutoff frequency.

16. The fluidic system of claim 15, wherein the cutoff frequency is less than or equal to 10 Hz.

17. A fluidic system for allow cytometer comprising:
    a fluidic pump;
    a fluidic channel;
    a first fluidic device adapted to attenuate pulsations with a shallow rolloff slope; and
    a second fluidic device adapted to attenuate pulsations with a shallow rolloff slope;
    wherein the first fluidic device and the second fluidic device are connected to the fluidic channel such that they cooperatively attenuate pulsations with a steep rolloff slope;
    wherein the first fluidic device includes a first fluidic resistor and a first fluidic capacitor, and wherein the second fluidic device includes a second fluidic resistor and a second fluidic capacitor.

18. The fluidic system of claim 17, wherein the pulsation attenuator is arranged in the following order: (1) first fluidic resistor, (2) first fluidic capacitor, (3) second fluidic resistor, and (4) second fluidic capacitor.

19. A fluidic system for allow cytometer comprising:
a fluidic pump;
a fluidic channel;
a first fluidic device adapted to attenuate pulsations with a shallow rolloff slope; and
a second fluidic device adapted to attenuate pulsations with a shallow rolloff slope;
wherein the first fluidic device and the second fluidic device are connected to the fluidic channel such that they cooperatively attenuate pulsations with a steep rolloff slope;
wherein the first fluidic device is adapted to attenuate pulsations with a rolloff slope of less than or equal to 20 dB/decade, and the second fluidic device is adapted to attenuate pulsations with a rolloff slope of less than or equal to 20 dB/decade.

20. The fluidic system of claim 19, wherein the first fluidic device and the second fluidic device are connected to the fluidic channel such that they cooperatively attenuate pulsations with a rolloff slope greater than 20 dB/decade.

21. A fluidic system for a flow cytometer comprising: a fluidic pump and the pulsation attenuator of claim 2.

22. The fluidic system of claim 21 wherein the pump is a peristaltic pump.

23. A fluidic system for a flow cytometer comprising: a fluidic pump and the pulsation attenuator of claim 4.

24. The fluidic system of claim 23 wherein the pump is a peristaltic pump.

25. A fluidic system for a flow cytometer comprising: a fluidic pump and the pulsation attenuator of claim 10.

26. The fluidic system of claim 25 wherein the pump is a peristaltic pump.

* * * * *